United States Patent
Khosravi

(10) Patent No.: US 6,221,091 B1
(45) Date of Patent: *Apr. 24, 2001

(54) COILED SHEET VALVE, FILTER OR OCCLUSIVE DEVICE AND METHODS OF USE

(75) Inventor: Farhad Khosravi, San Mateo, CA (US)

(73) Assignee: Incept LLC, San Mateo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/318,492

(22) Filed: May 25, 1999

Related U.S. Application Data

(63) Continuation of application No. 08/942,033, filed on Sep. 26, 1997, now Pat. No. 5,925,063.

(51) Int. Cl.[7] .................................................. A61M 29/00
(52) U.S. Cl. .......................................... 606/200; 623/1.24
(58) Field of Search ........................... 606/200, 190–198; 623/1.12, 1.24–1.26, 2.13–2.19, 23.64–23.7, 2; 3/1.5

(56) References Cited

U.S. PATENT DOCUMENTS

| | | | |
|---|---|---|---|
| 4,218,782 | * 8/1980 | Rygg | 3/1.5 |
| 4,425,908 | 1/1984 | Simon | 128/1 R |
| 4,624,822 | * 11/1986 | Arru et al. | 264/544 |
| 4,662,885 | 5/1987 | DiPisa, Jr. | 623/12 |
| 4,665,918 | 5/1987 | Garza et al. | 128/343 |
| 4,705,517 | 11/1987 | DiPisa, Jr. | 623/12 |
| 4,723,549 | 2/1988 | Wholey et al. | 128/344 |
| 4,794,927 | 1/1989 | Yoon | 128/326 |
| 5,007,926 | 4/1991 | Derbyshire | 623/1 |
| 5,382,261 | 1/1995 | Palmaz | 606/158 |
| 5,409,019 | 4/1995 | Wilk | 128/898 |
| 5,443,500 | 8/1995 | Sigwart | 623/1 |
| 5,509,930 | * 4/1996 | Love | 623/2 |
| 5,578,075 | * 11/1996 | Dayton | 623/1 |
| 5,618,299 | * 4/1997 | Khosravi et al. | 606/198 |
| 5,655,548 | 8/1997 | Nelson et al. | 128/898 |
| 5,800,525 | 9/1998 | Bachinski et al. | 623/1 |
| 5,824,046 | 10/1998 | Smith et al. | 623/1 |
| 5,824,054 | * 10/1998 | Khosravi et al. | 623/1 |
| 5,925,063 | * 7/1999 | Khosravi | 606/200 |
| 5,938,683 | * 8/1999 | Lefebvre | 606/200 |
| 5,976,172 | * 11/1999 | Homsma et al. | 606/200 |

FOREIGN PATENT DOCUMENTS

WO 99/15224 * 4/1999 (WO) ........................... A61M/29/00

* cited by examiner

Primary Examiner—Gary Jackson
Assistant Examiner—Jonathan D. Goldberg
(74) Attorney, Agent, or Firm—Fish & Neave; Nicola A. Pisano

(57) ABSTRACT

Apparatus is provided comprising a coiled sheet having a plurality of flaps mounted on its interior surface that project radially inward into a lumen formed by the interior surface of the apparatus when it is deployed. The flaps lie parallel to the interior surface of the sheet during transluminal delivery, but project radially inward once the apparatus is deployed. The flaps may comprise a fine mesh for use as a filter, or alternatively may be covered with a biocompatible material that is substantially impermeable, so as to partially or completely occlude the lumen. In a further alternative embodiment, the flaps may comprise a resilient biocompatible plastic or polymer, so that the flaps move in response to the flow and function as a pressure-based or directional valve.

20 Claims, 2 Drawing Sheets

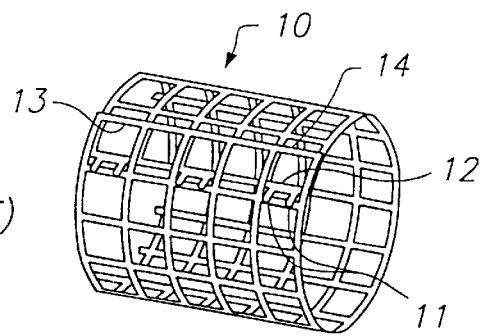
FIG. 1
(PRIOR ART)
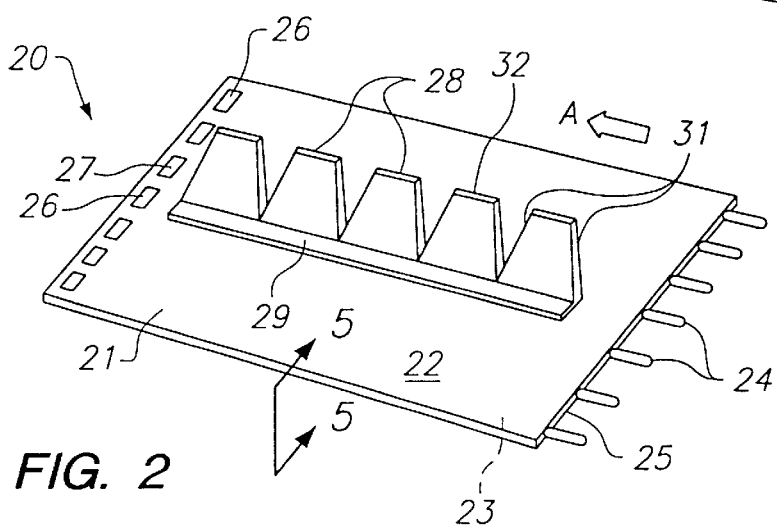
FIG. 2
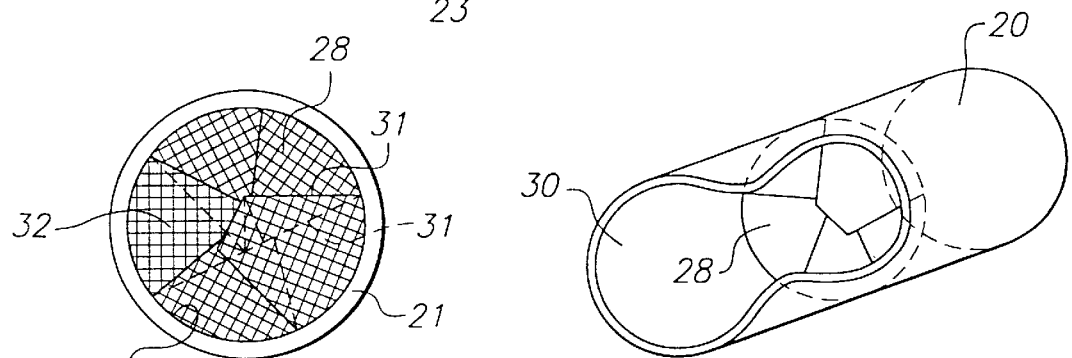
FIG. 4A
FIG. 3
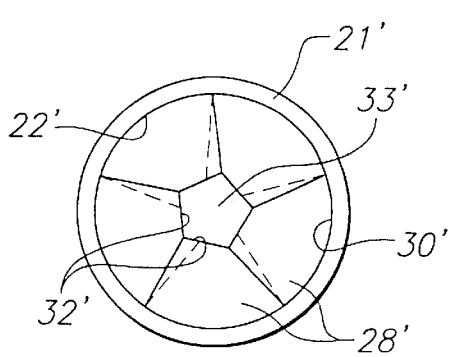
FIG. 4B
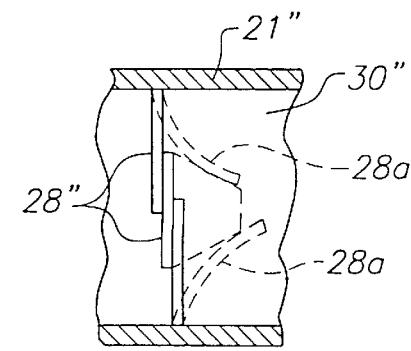
FIG. 4C

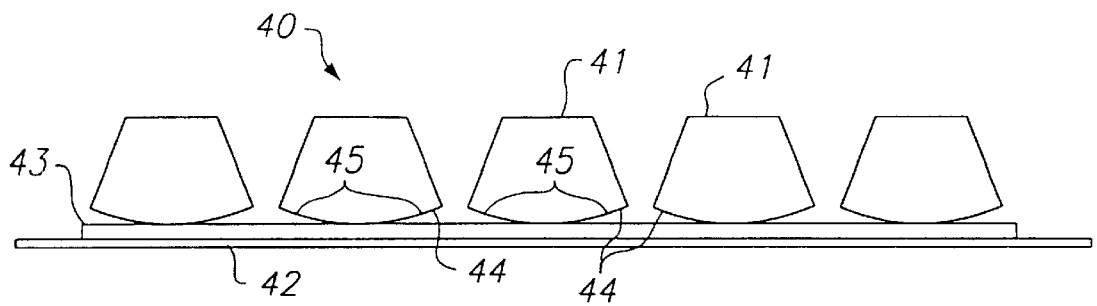
FIG. 5A
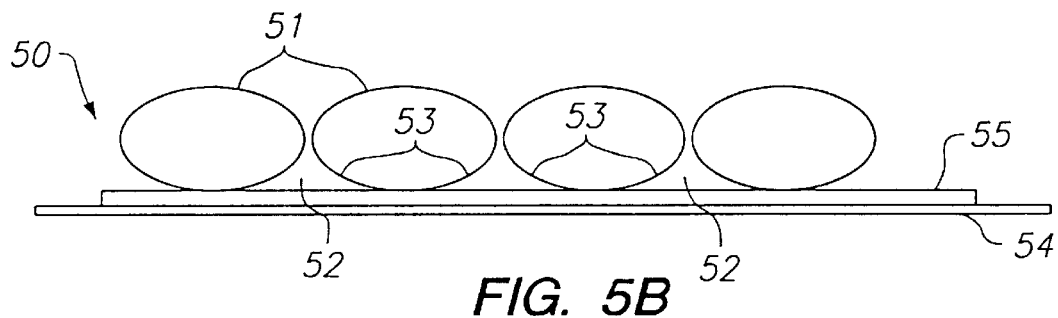
FIG. 5B
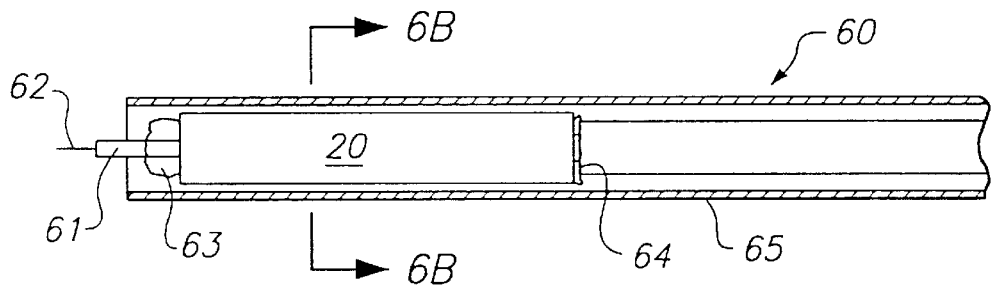
FIG. 6A
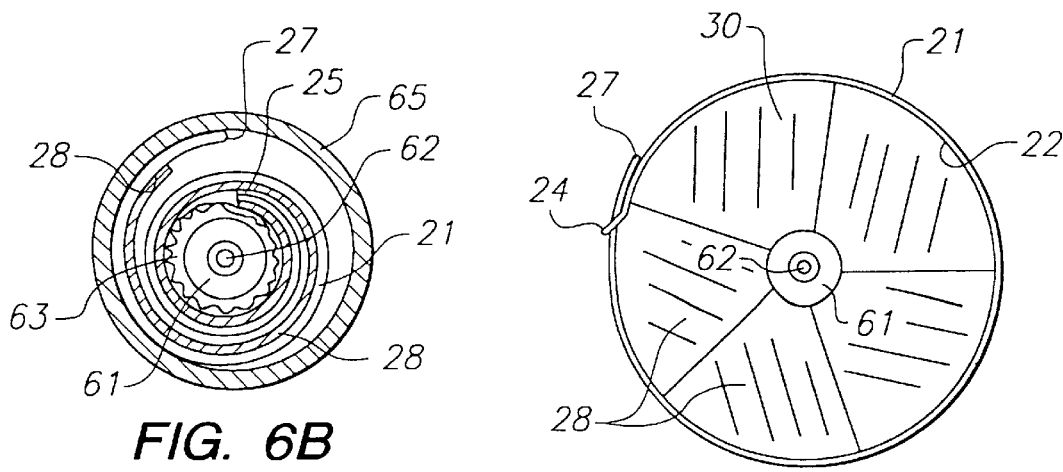
FIG. 6B
FIG. 6C

COILED SHEET VALVE, FILTER OR OCCLUSIVE DEVICE AND METHODS OF USE

This application is a Continuation of U.S. Ser. No. 08/942,033 filed Sep. 26, 1997 now U.S. Pat. No. 5,925,063.

FIELD OF THE INVENTION

The present invention relates generally to minimally-invasive techniques and apparatus for implanting a filter, valve or occlusive device in a hollow-body organ or vessel.

BACKGROUND OF THE INVENTION

In recent years a need has arisen for filters, valves and occlusive devices that may be implanted percutaneously and transluminally. Such devices may be used either to filter particulate matter from a fluid flow, to regulate the fluid flow, or to partially or completely occlude the flow.

A number of devices are known for trapping particulate matter downstream of the site of a therapeutic procedure, e.g., angioplasty, to reduce embolization of materials following completion of the procedure. U.S. Pat. No. 4,723,549 to Wholey et al. describes a filter basket disposed from an angioplasty device to collect and trap frangible material liberated during an angioplasty procedure. U.S. Pat. No. 4,425,908 describes an implantable self-expanding filter basket formed of a plurality of nickel-titanium wires.

A number of devices also are known for occluding flow through a vessel. For example, U.S. Pat. No. 5,382,261 to Palmaz is directed to a deformable slotted stent that includes a membrane disposed transverse to the flow direction to occlude the vessel. These devices may be advantageously used wherever it is desired to occlude flow, for example, through a arterio-venous fistula, or as part of the treatment of a congenital heart defect.

A number of devices also are known for regulating the flow of tissue through a body vessel or organ. U.S. Pat. No. 5,655,548 to Nelson et al. describes a tubular member including a valved portion for regulating the flow through an arterio-venous passageway. U.S. Pat. No. 5,409,019 to Wilk describes regulating flow through a myocardial passageway using a first embodiment comprising a multi-part rigid stent that includes valve flaps, and an alternative embodiment wherein the stent itself is biased to collapse during cardiac diastole.

A drawback of the foregoing devices is that they generally are not compatible with previously known delivery devices, and require special handling for optimum performance. In addition, such devices have a limited range of applications in which they may be employed. Specifically, the ability to deliver such devices to small diameter vessels depends on the specific configuration of the device and its intended purpose.

A stent design particularly well suited for use as a base for a filter, valve or occluder is the coiled sheet stent of the type described in U.S. Pat. No. 5,007,926 to Derbyshire, and U.S. Pat. No. 5,443,500 to Sigwart, which are incorporated herein by reference. A coiled sheet stent generally comprises a flat relatively flexible mesh, and may have teeth on one edge and openings that accept the teeth on the opposing edge. The stent is formed by rolling the mesh into a tube, with the edge oriented inside and aligned with the axis of the tube. The stent generally is formed of a resilient material, such as stainless steel or a nickel-titanium alloy, and may be designed to be highly crush resistant.

The foregoing coiled sheet stents may be percutaneously and transluminally delivered by rolling the stent to a small diameter and inserting it into a sheath that retains the stent in the contracted state. Such a delivery system is described in U.S. Pat. No. 4,665,918 to Garza et al., which is also incorporated herein by reference. Upon delivery of a coiled sheet stent to the implantation site, the constraint (e.g., sheath) is removed, and the stent is permitted to unroll. The stent may be further expanded into position using a conventional balloon dilatation device, thereby locking the teeth into engagement with the openings in the opposing edge.

In view of the foregoing, it would be desirable to provide apparatus that may be delivered using previously known delivery apparatus, and that can be delivered to small vessels and through tortuous vessel anatomy.

It further would be desirable to provide a device capable of being employed as either a filter, a valve or occluder, depending upon the desired therapeutic application.

It also would be desirable to provide a device capable of being employed in filter, valve or occluder applications that builds upon the acknowledged advantages of coiled sheet stent technology, including capability to achieve very small delivery diameters, ease of deployment, high crush resistance, and low migration potential.

SUMMARY OF THE INVENTION

In view of the foregoing, it is an object of this invention to provide apparatus suitable for use in filter, flow regulation, and occlusion applications that overcomes the drawbacks of previously known devices.

It is a further object of the present invention to provide apparatus that may be delivered using previously known delivery apparatus, and that can be delivered to small vessels and through tortuous vessel anatomy.

It is another object of this invention to provide a device capable of being employed as either a filter, a valve or occluder, depending upon the desired therapeutic application.

It is a still further object of the present invention to provide a device capable of being employed in filter, valve or occluder applications that builds upon the acknowledged advantages of coiled sheet stent technology, including capability to achieve very small delivery diameters, ease of deployment, high crush resistance, and low migration potential.

These and other objects of the invention are accomplished in accordance with the principles of the invention by providing apparatus comprising a coiled sheet having a plurality of flaps mounted on its interior surface, the flaps projecting radially inward into a lumen formed by the interior surface of the apparatus when it is deployed. In accordance with the invention, the flaps lie parallel to the interior surface of the coiled sheet when the apparatus is configured for delivery, and project radially inward once the apparatus is deployed.

In one embodiment of the invention, the flaps are formed of a fine mesh, and are arranged so that the innermost ends of the tips overlap when the apparatus is deployed. The flaps may in addition be coated with an anti-thrombogenic material (e.g. heparin), for improved hemo-compatibility. In this case, the mesh serves to filter particulate matter from the flow passing through the apparatus, thus reducing the risk of embolism.

Alternatively, the flaps may be covered with a biocompatible material that is substantially impermeable. If the tips of the flaps are configured to overlap, the device may be used as an occlusive device to completely cut-off the flow through the central lumen of the apparatus. If, on the other hand, the tips of the flaps do not overlap, they may form an aperture having a reduced diameter (relative to the vessel diameter), to provide a degree of flow regulation.

In yet a further alternative embodiment, the flaps may comprise a resilient biocompatible plastic or polymer, so that the flaps move in response to the flow. In this embodiment, the flaps may advantageously serve as a valve that actively regulates flow through the vessel or organ.

In accordance with the principles of the present invention, a filter, valve or occlusive apparatus constructed in accordance with the present invention employs a coiled sheet stent as the base for delivering and implanting the device. Such stents generally have high crush resistance, and the use of interlocking teeth, as in the above-incorporated Derbyshire and Sigwart patents, reduces the risk of post implantation migration. These benefits are directly transferred to a device constructed in accordance with the present invention, as well as small delivery diameter and ease of use.

Methods for employing a device constructed in accordance with the principles of the present invention are also described.

BRIEF DESCRIPTION OF THE DRAWINGS

Further features of the invention, its nature and various advantages will be more apparent from the accompanying drawings and the following detailed description of the preferred embodiments, in which:

FIG. 1 is a perspective view of a previously known coiled sheet stent suitable for use in constructing the apparatus of the present invention;

FIG. 2 is a perspective view of apparatus constructed in accordance with the present invention in an unrolled state;

FIG. 3 is a perspective view, partly cut-away, of the apparatus of FIG. 2 in its deployed condition;

FIGS. 4A, 4B and 4C are sectional views showing alternative embodiments of the flaps of the present invention;

FIGS. 5A and 5B are views similar to that taken along line 5—5 of FIG. 2 illustrating alternative embodiments of the flaps of the apparatus of the present invention; and FIGS. 6A and 6B are, respectively, an elevation view, partly in section, and cross-sectional view showing the apparatus of FIG. 2 loaded with a delivery device, while FIG. 6C illustrates a step of deploying the apparatus.

DETAILED DESCRIPTION OF THE INVENTION

The present invention provides apparatus capable of serving as a filter, a valve or an occlusive device which can be percutaneously and transluminally implanted within a body vessel or organ. In particular, the apparatus comprises a coiled sheet having a plurality of radially inwardly projecting flaps that project into a lumen formed in the apparatus when it is deployed. The tips of the flaps may be arranged to overlap, so that if the flaps comprise a mesh, the flaps form a filter that traps particulate matter flowing through the lumen.

Alternatively, the flaps may be covered with an impermeable biocompatible material that occludes flow through the vessel. The flaps, may also be covered with an impermeable biocompatible material and have non-overlapping tips, thereby forming an aperture that introduces a passive flow impedance. In yet another embodiment the flaps may comprise a resilient plastic or polymer, and function as parts of a valve, thus providing active flow regulation.

Advantageously, the apparatus of the present invention may be configured to provide a variety of functions, while retaining some of the best characteristics of a coiled sheet stent, such as small delivery diameters, high crush resistance, low migration potential and ease of deployment.

Referring now to FIG. 1, a previously known coiled sheet stent 10 is described. Coiled sheet stent 10 is of the type described in U.S. Pat. No. 5,007,926 to Derbyshire and U.S. Pat. No. 5,443,500 to Sigwart, which are incorporated herein by reference. Coiled sheet stent 10 generally comprises a mesh formed of a flexible material such as a stainless steel or nickel-titanium alloy. Stent 10 preferably includes teeth 11 on edge 12 and openings 13 on opposing edge 14 that engage teeth 11 when the stent is deployed. Stent 10 is formed by rolling the mesh into a tube, with edge 12 positioned inside and aligned with the axis of the tube.

Stent 10 may be percutaneously and transluminally delivered by rolling the stent to a small diameter and inserting it into a sheath that retains the stent in a contracted delivery state. Such a delivery system is described in the above-incorporated Sigwart patent and in U.S. Pat. No. 4,665,918 to Garza et al., which is also incorporated herein by reference. Upon delivery of stent 10 to the implantation site, the sheath is retracted, and the stent is permitted to uncoil. The stent may be further expanded into position using a conventional balloon dilatation device, so that teeth 11 engage openings 13 to lock the stent in its deployed state.

Referring now to FIG. 2, illustrative apparatus constructed in accordance with the present invention is described. Apparatus 20 comprises flat sheet 21 of biocompatible material typically used in coiled sheet stents having upper surface 22 and lower surface 23. For clarity, the details of sheet 21 are omitted. Apparatus 20 preferably includes teeth 24 on longitudinal edge 25 and openings 26 on opposing longitudinal edge 27 that accept teeth 24 when the apparatus 20 is rolled into its deployed state. In accordance with the present invention a plurality of flaps 28 are affixed to upper surface 22 of sheet 21, and project upward from the sheet when unconstrained. Flaps 28 may be affixed to flat sheet 21 along marginal portion 29 using any suitable means, including welding, brazing or the use of a suitable biocompatible adhesive. Alternatively, flaps 28 may be individually attached to sheet 21 without marginal portion 29.

In FIG. 3, apparatus 20 is shown in a deployed configuration, wherein the sheet is rolled in the direction of arrow A about longitudinal edge 25 to form a tubular member. When rolled to the tubular configuration shown in FIG. 3, upper surface 22 forms lumen 30 into which flaps 28 project radially inward. Depending upon the length, shape, and composition of flaps 28, apparatus 20 may be configured to provide either a filter, flow regulator or valve, or an occlusive device.

Referring to FIG. 4A, an embodiment is depicted wherein flaps 28 are sized so that when the apparatus is arranged in its deployed configuration, edges 31 and tips 32 of the flaps overlap one another. In this case, flaps 28 extend over the entire cross-section of lumen 30. Preferably, the flaps are interdigitated in a manner similar to a camera-lens iris, so that each flap supports its neighboring flaps. In this embodiment, flaps 28 may be constructed of a fine mesh material, e.g., a stainless steel or nickel-titanium alloy, so that when deployed they form a filter. Thus, for example, apparatus 20 may be advantageously deployed in a blood vessel prior to a therapeutic procedure, such as angioplasty, or endarterectomy, to capture any frangible material liberated during the procedure. When employed as a blood filter, the mesh comprising flaps 28 may in addition be coated or impregnated with an anti-thrombogenic agent, such as heparin.

Alternatively, flaps 28 may be coated with a layer of fluid impermeable material, for example, polytetrafluoroethylene (PTFE) or polyurethane. In this case, when flaps 28 are deployed, they occlude flow through lumen 30. In addition, the flaps may be coated or impregnated with a thrombogenic agent, to cause further clotting off of the vessel or organ.

Referring to FIG. 4B, an alternative embodiment is shown in which tips 32' of flaps 28' do not overlap when the flaps are deployed. Instead, the flaps project from interior surface 22' of the apparatus a distance less than the radius of the apparatus in the deployed configuration. Accordingly, when flaps 28' are deployed in lumen 30', tips 32' form an aperture 33'. In this case, flaps 28' may again be coated with a fluid impermeable material, such as PTFE or urethane. Because aperture 33' is smaller than the diameter of lumen 30', flaps 28' will create an impedance to flow passing through the apparatus, thereby providing a degree of passive flow regulation. The flow regulation is passive in the sense that it is the pressure differential created by the aperture that assists in regulating the flow, while flaps 28' remain stationary.

In the alternative embodiment depicted in FIG. 4C, flaps 28" are formed of a pliable plastic or polymeric material, either alone or coated over a flexible wire mesh. In this embodiment, the composition of flaps 28" is selected so that the flaps form a valve that actively regulates flow through the vessel by moving. For example, flaps 28" may be constructed to open, for example, when the pressure differential across the flaps exceeds a predetermined value. This aspect of the invention is shown by the dotted lines 28a in FIG. 4C. Alternatively, flaps 28" may be biased in one direction to provide a one-way valve, whereby flaps 28" open when flow is moving in one direction, but close off lumen 30" when the flow moves in the opposite direction. Such an embodiment may be advantageously employed, for example, in the above-described patents to Nelson et al. and Wilk.

In FIGS. 5A and 5B, further alternative embodiments of the apparatus of the present invention are shown from an edge-on perspective. In FIG. 5A, apparatus 40 is described having flaps 41 that are approximately trapezoidal in shape, as in the embodiment of FIG. 2, which are affixed to sheet 42. In FIG. 5A, however, the bases of the flaps are not joined along their lengths to marginal portion 43. Instead, the bases include cut-out areas 44. The curved edges 45 of cut-out areas 44 approximate the curvature of the coiled sheet when it is rolled to its deployed to deployed configuration. Applicant expects that the inclusion of cut-out areas 44 in apparatus 40 will reduce the tendency of the flaps to cause the device to assume an out-of-round shape when deployed.

In apparatus 50 of FIG. 5B, flaps 51 are ellipsoidal in shape, and include cut-out areas 52 having curved edges 53 that approximate the curvature of the deployed apparatus. Flaps 51 are joined to sheet 54 by marginal portion 55. The ellipsoidal shape of flaps 51, like the trapezoidal shapes of flaps 28 and 41, are intended to be illustrative only. One of skill in the art of designing interventional implantable devices will readily recognize that the flaps used in a device constructed in accordance with the present invention could take any shape, so long as when the flaps are deployed they provide a beneficial therapeutic effect, e.g., as a filter, valve or occlusive device. For example, different ones of the plurality of flaps 28 may have different sizes, or may even comprise different materials.

Likewise, the precise number of flaps employed may vary depending upon the intended application. For smaller vessels, e.g., 3–5 mm, as few as two flaps may be used to provide a filter, valve or occlusive device. In larger vessels, e.g., up to 3 cm, it may be desirable to employ a greater number of flaps. It is therefore to be understood that the use in the above-described embodiments of four and five flaps, respectively, is intended only for purposes of illustration, and that a greater or fewer number of flaps may be employed depending upon the specific application.

Referring now to FIGS. 6A to 6C, apparatus 20 of FIG. 2 is shown disposed within a delivery device in its contracted state. Delivery device 60 illustratively includes shaft 61 including a lumen for guidewire 62, inflatable balloon 63 and shoulder 64 of shaft 61, which contacts the proximal edge of apparatus 20. Delivery device 60 further includes outer sheath 65 that retains apparatus 20 in the contracted state. Delivery device 60 may be constructed by modifying the delivery system described in the above-incorporated Sigwart patent, or U.S. Pat. No. 4,665,918 to Garza et al., which is incorporated herein by reference.

As shown in FIG. 6B, apparatus 20 is contracted for delivery by bending flaps 28 so that they lie flat against interior surface 22, and then rolling flat sheet 21 from edge 25 toward edge 27. Apparatus 20 is then placed over inflatable balloon 63 of delivery device 60, and outer sheath 65 advanced to retain apparatus 20 in its contracted state. Alternatively, apparatus 20 may be directly wrapped around inflatable balloon 63 of shaft 61 with the outer sheath retracted, and the outer sheath is then advanced to retain apparatus 20 in position.

When apparatus 20 is rolled down to its contracted delivery state, flaps 28 offer little resistance to rolling sheet 21 down tightly. When delivery device 60 is percutaneously and transluminally positioned at the site where the apparatus is to be deployed, outer sheath 65 is retracted proximally. As outer sheath 65 is retracted, shoulder 64 prevents proximal movement of apparatus 20.

As shown in FIG. 6C, when outer sheath 65 clears the proximal end of the coiled sheet, sheet 21 expands radially outward into contact with the interior of the wall of the vessel or body organ (not shown). Because flaps 28 are resiliently biased to project from interior surface 22 of sheet 21, they begin to project radially outward into lumen 30 as soon as coiled sheet assumes its expanded diameter. Next, inflatable balloon 63 is inflated to lock teeth 24 into engagement with openings 26 in edge 27 at a desired expanded diameter. Balloon 63 is then deflated and delivery device 60 is withdrawn from the patient's body. As delivery device 60 is retracted from within lumen 30 of apparatus 20, flaps 28 resiliently assume a position substantially orthogonal to the interior surface of the coiled sheet.

The methods and apparatus of the present invention have been described with reference to filtering, regulating flow within, or occluding blood vessels, and organs. The apparatus of the present invention is equally applicable to gastrointestinal, respiratory, reproductive organ and urethral applications and elsewhere where is desirable to filter, regulate or occlude flow through an organ or vessel.

While preferred illustrative embodiments of the present invention are described above, it will be apparent to one skilled in the art that various changes and modifications may be made therein without departing from the invention and it is intended in the appended claims to cover all such changes and modifications which fall within the true spirit and scope of the invention.

What is claimed is:

1. A method of altering flow through a vessel or body organ, the method comprising:

providing apparatus comprising a sheet having an interior surface, and a plurality of flaps disposed from the interior surface;

providing a delivery device comprising a sheath with a lumen, a shaft with an exterior surface, and an inflatable balloon disposed around the exterior surface of the shaft, the shaft and inflatable balloon disposed within the lumen;

rolling the sheet to form a tubular member in a delivery state of reduced diameter suitable for transluminal delivery, the interior surface defining a lumen of the tubular member, the flaps lying substantially parallel to the lumen;

placing the tubular member in the delivery state within the lumen and around an exterior surface of the balloon;

positioning the delivery device in the vessel or organ percutaneously and transluminally; and expanding the apparatus, the tubular member assuming a deployed state of expanded diameter wherein the tubular member sealingly engages an interior wall of the vessel or organ, the flaps projecting radially inward into the lumen to alter flow through the vessel or organ.

2. The method of claim 1, wherein expanding the apparatus comprises retracting the sheath proximally to radially expand the tubular member to the deployed state.

3. The method of claim 1 further comprising:

inflating the balloon so that the tubular member sealingly engages the interior wall;

deflating the balloon; and removing the delivery device from the vessel or organ, the flaps projecting radially inward.

4. The method of claim 3, wherein the sheet comprises first and second longitudinal edges, a plurality of teeth arranged along the first edge, and a plurality of openings arranged along the second edge.

5. The method of claim 4, wherein inflating the balloon further comprises engaging the plurality of openings with the plurality of teeth.

6. The method of claim 1, wherein the plurality of flaps comprise a fluid permeable mesh.

7. The method of claim 6, wherein expanding the apparatus further comprises:

spanning a cross section of the lumen of the tubular member with the plurality of flaps; and filtering flow through the vessel or organ with the fluid permeable mesh.

8. The method of claim 7, wherein providing apparatus further comprises providing a coating of an anti-thrombogenic agent, the coating disposed on the plurality of flaps.

9. The method of claim 1, wherein the plurality of flaps comprise a fluid impermeable material.

10. The method of claim 9, wherein expanding the apparatus further comprises:

spanning a cross section of the lumen of the tubular member with the plurality of flaps; and occluding flow through the vessel or organ with the fluid impermeable material.

11. The method of claim 10, wherein providing apparatus further comprises providing a coating of an anti-thrombogenic agent, the coating disposed on the plurality of flaps.

12. The method of claim 11, wherein expanding the apparatus further comprises:

defining an aperture with the plurality of flaps, the aperture having a smaller diameter than the expanded diameter of the lumen of the tubular member; and regulating flow through the vessel or organ with the tips of the flaps.

13. The method of claim 9, wherein each of the plurality of flaps has a tip.

14. The method of claim 1 wherein the plurality of flaps comprise a resilient material capable of deflecting.

15. The method of claim 14, wherein expanding the apparatus further comprises forming a valve with the plurality of flaps, the valve opening when flow through the vessel or organ moves in a first direction and closing when flow moves in a second direction opposite the first direction.

16. The method of claim 1, wherein the flaps have a trapezoidal shape.

17. The method of claim 1, wherein:

each of the plurality of flaps has cut out areas near a point of attachment of the flap to the sheet; and expanding the apparatus further comprises aligning the cutout areas along a curvature of the tubular member.

18. The method of claim 1, wherein the sheet comprises a nickel-titanium alloy.

19. The method of claim 1, wherein the sheet comprises first and second longitudinal edges, a plurality of teeth arranged along the first edge, and a plurality of openings arranged along the second edge.

20. The method of claim 19, wherein expanding the apparatus further comprises engaging the plurality of openings with the plurality of teeth.

* * * * *